(12) United States Patent
Nagatsu

(10) Patent No.: US 7,700,039 B2
(45) Date of Patent: Apr. 20, 2010

(54) MICROWAVE PLASMA STERILIZING METHOD AND DEVICE

(75) Inventor: Masaaki Nagatsu, Shizuoka (JP)

(73) Assignee: Japan Science and Technology Agency, Saitama (JP)

(*) Notice: Subject to any disclaimer, the term of this patent is extended or adjusted under 35 U.S.C. 154(b) by 755 days.

(21) Appl. No.: 10/593,325

(22) PCT Filed: Mar. 15, 2005

(86) PCT No.: PCT/JP2005/005058

§ 371 (c)(1),
(2), (4) Date: Sep. 18, 2006

(87) PCT Pub. No.: WO2005/089818

PCT Pub. Date: Sep. 29, 2005

(65) Prior Publication Data

US 2007/0212254 A1    Sep. 13, 2007

(30) Foreign Application Priority Data

Mar. 19, 2004   (JP) ............................. 2004-081733

(51) Int. Cl.
  *A61L 2/12* (2006.01)
  *A61L 2/14* (2006.01)
(52) U.S. Cl. ........................................ 422/21; 422/243
(58) Field of Classification Search .................... 422/21, 422/243, 244, 305
See application file for complete search history.

(56) References Cited

U.S. PATENT DOCUMENTS 3,851,436 A    12/1974   Fraser et al.
3,948,601 A    4/1976    Fraser et al.
4,931,261 A    6/1990    Jacob
5,512,244 A    4/1996    Griffiths et al.
5,619,020 A    4/1997    Jones et al.

(Continued)

FOREIGN PATENT DOCUMENTS

JP    46-8075 A    6/1971

(Continued)

OTHER PUBLICATIONS

International Search Report, PCT/JP 2005/005058 (Jun. 2005).

*Primary Examiner*—John Kim
(74) *Attorney, Agent, or Firm*—Rader, Fishman & Grauer, PLLC

(57) ABSTRACT

A microwave inlet for introducing microwaves (coaxial waveguide) and a microwave launcher for generating volume-wave plasma are arranged on one side in a vacuum chamber, and a movable metal plate is arranged opposite to the microwave launcher on the other side in the vacuum chamber. The microwave launcher has a sandwiched structure where a quartz plate is sandwiched by a perforated plate having many holes of a specified diameter. Microwaves are introduced from an external microwave generator to the microwave launcher in, for example, oxygen gas, a mixture of helium gas and oxygen gas, a mixture of argon gas and oxygen gas, or a mixture of oxygen gas and nitrogen gas to change the spatial distribution of the electric field intensity, whereby the volume-wave plasma discharge is diffused to the entire inner space of the vacuum chamber by microwaves leaking through the holes in the perforated plate. The sterilizing method and the device of this invention use microwave discharge plasma that enables sterilization inside a perforated resinous package, such as a package of medical instruments in a vacuum chamber.

10 Claims, 9 Drawing Sheets

U.S. PATENT DOCUMENTS

| | | | |
|---|---|---|---|
| 5,633,424 A * | 5/1997 | Graves et al. | 422/22 |
| 6,149,878 A | 11/2000 | Jacob et al. | |
| 6,565,791 B1 * | 5/2003 | Laurent | 264/455 |

FOREIGN PATENT DOCUMENTS

| | | |
|---|---|---|
| JP | 48-65796 A | 9/1973 |
| JP | 61-11049 A | 1/1986 |
| JP | 63-89162 A | 4/1988 |
| JP | 01-502883 A | 10/1989 |
| JP | 02-279160 A | 11/1990 |
| JP | 05-229530 A | 9/1993 |
| JP | 06-505171 A | 6/1994 |
| JP | 06-263120 A | 9/1994 |
| JP | 08-119236 A | 5/1996 |
| JP | 08-143012 A | 6/1996 |
| JP | 10-129627 A | 5/1998 |
| JP | 11-501530 A | 2/1999 |
| JP | 11-505166 A | 5/1999 |
| JP | 11-506677 A | 6/1999 |
| JP | 11-278444 A | 10/1999 |
| JP | 2000-308675 A | 11/2000 |
| JP | 2000-316954 A | 11/2000 |
| JP | 2001-149918 A | 6/2001 |
| JP | 2001-326216 A | 11/2001 |
| JP | 2002-102313 A | 4/2002 |
| JP | 2002-536071 A | 10/2002 |
| JP | 2003-135571 A | 5/2003 |
| JP | 2004-267524 A | 9/2004 |
| WO | WO00/45861 A | 8/2000 |

* cited by examiner

MICROWAVE PLASMA STERILIZING METHOD AND DEVICE

FIELD OF THE INVENTION

This invention relates to a sterilizing method and device. Specifically, this invention relates to a sterilizing method and device using microwave plasma for disinfection and sterilization of medical instruments contained in resinous packages and for sterilization of foods in packages and bags for foods.

BACKGROUND ART

Conventional disinfection and sterilization methods for medical instruments and disinfection methods for foods in packages and bags for foods include dry-heat sterilization, steam under pressure sterilization, radiosterilization, ethylene oxide gas sterilization and plasma sterilization.

Dry-heat sterilization uses high temperatures of 160 to 180° C. or above and this application is limited to metal and glass products. Sixty minutes are required to complete dry-heat sterilization. Steam under pressure sterilization also uses high temperatures and these applications are also limited to metal and glass products. Twenty minutes are required to complete steam under pressure sterilization. Moreover, this method cannot be used for humidity-sensitive materials (such as paper). Radiosterilization has the risk of a health hazard to the human body. Radiosterilization is not effective to areas where the radiation does not reach. Ethylene oxide gas sterilization requires very careful handling due to the toxicity and flammability of the gas used. The difficult disposal of residual materials after sterilization also poses a problem.

Various plasma sterilization techniques have been announced including, for example, the Publication of Unexamined Utility Model Application No. 57352-1994 and the Publication of Unexamined Patent Application No. 135571-2003. In principle, most of them use a high temperature to sterilize and as such involve handling problems. Some techniques use inert gases such as argon gas and chlorine gas in vacuum to generate gas plasma using a high-frequency power supply to sterilize the target objects. Chlorine gas is toxic and plasma occurs on the surface of the discharging electrode, and is not effective.

As described above, conventional plasma sterilization techniques use surface-wave plasma. The inside of a package is difficult to sterilize and as such sterilization is limited to the exterior of the package. These techniques are not applicable to resinous medical instruments such as catheters and injection devices and medical instruments that require sterilization of their insides such as vacuum tubes for drawing blood. The objects that can be sterilized are also limited due to thermal problems related to plasma irradiation. Other sterilization methods have various limitations and hazards due to their use of high temperature, high pressure and toxic gas. There has been a growing demand for a sterilization method that uses low temperature, low pressure and safe procedures and is capable of high-speed sterilization.

DISCLOSURE OF THE INVENTION

This invention provides a plasma sterilization method and device using volume-wave plasma excited by microwave pulses in, for instance, oxygen gas in place of conventional surface-wave plasma.

To attain the above objective, the first invention provides a microwave plasma sterilizing device comprising a microwave generator for outputting pulsed microwaves and a vacuum chamber with a gas inlet, outlet for a pump and for opening and closing the plate; wherein the microwave inlet for introducing the microwaves and a microwave launcher of the sandwiched structure where the quartz plate for generating volume-wave plasma is sandwiched by a stainless steel perforated plate are arranged on one side in said vacuum chamber, and a movable metal plate is arranged opposite to said microwave launcher on the other side in said vacuum chamber; wherein said movable metal plate is connected to an elevating means to allow vertical positional adjustment and wherein the object being sterilized is placed between said microwave launcher and said movable metal plate.

EFFECTS OF THE INVENTION

According to the microwave plasma sterilizing method and device of this invention, volume-wave plasma excited by microwave pulses using, for instance oxygen gas, is used in place of the surface-wave plasma used in conventional plasma sterilizing methods. It is possible to sterilize the inside of a package, and the inside of resinous medical instruments such as catheters, injection devices and vacuum tubes for drawing blood. The thermal problem caused by plasma irradiation is solved by using pulsed microwave, thereby avoiding any material change of the object being sterilized. This invention provides a sterilizing method and device capable of low-temperature, low-pressure and safe sterilization with high-speed processing time. The ultraviolet sterilization effect of nitrogen gas is added to the effective sterilization effect of etching due to oxygen radicals because a mixture of oxygen gas and nitrogen gas is used and introduced to the vacuum chamber. Furthermore, it is noteworthy that an effective sterilization effect is expected in a gas of a mixing ratio close to that of air.

The sandwiched structure of the microwave launcher, where the quartz plate is sandwiched by a stainless steel perforated plate, enables volume-wave plasma discharge. The thermal problem caused by plasma irradiation is solved by using pulsed microwaves, making it possible to sterilize objects inside packages.

BEST MODE FOR IMPLEMENTING THE INVENTION

Figure 1:
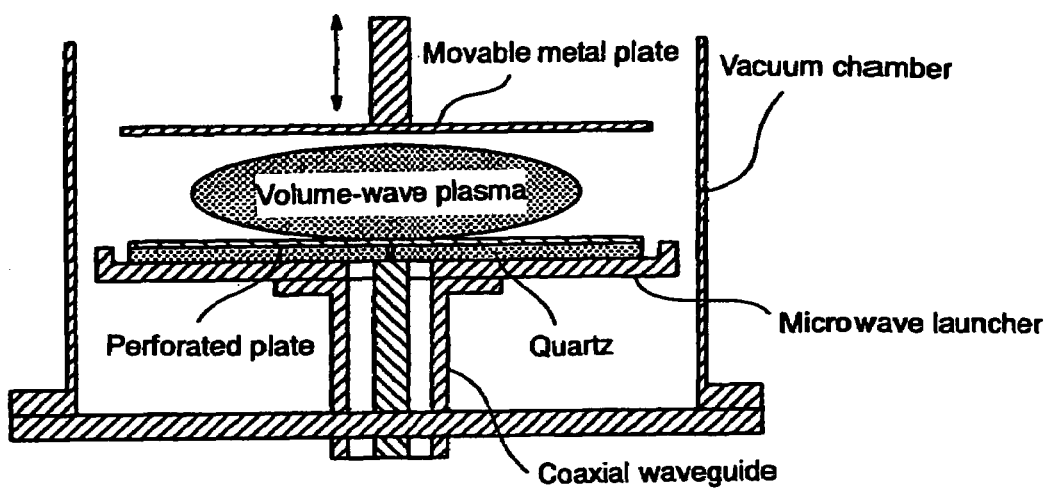
FIG. 1 is an explanatory drawing of the microwave plasma sterilizing device of this invention.

The embodiments of this invention are described below referring to the accompanying drawings. FIG. 1 shows a part of the microwave plasma sterilizing device of this invention. This figure is an explanatory drawing that describes plasma generation. The microwave inlet for introducing microwaves (coaxial waveguide) and a microwave launcher for generating volume-wave plasma are arranged on one side (the lower side in the figure) in the vacuum chamber, while a movable metal plate is arranged opposite to the microwave launcher on the other side (the upper side in the figure) in the vacuum chamber.

Said microwave launcher has a sandwiched structure where the quartz plate is sandwiched by a stainless steel perforated plate. Said movable metal plate is connected to an elevating means (not shown) that allows vertical positional adjustment. Said perforated plate is perforated with many holes of a specified diameter.

Microwaves are introduced from an external microwave generator (not shown) into the microwave launcher in the gas that produces an active species with a sterilization effect in the presence of plasma, such as in oxygen gas, a mixture of helium gas and oxygen gas, a mixture of argon gas or oxygen gas. The spatial distribution of the electric field intensity is controlled by setting the position of the metal plate arranged opposite to said microwave launcher to diffuse the volume-wave plasma discharge to the entire inner space of the vacuum chamber by the microwave leaking through the holes in the perforated plate.

This volume-wave plasma discharge is used to generate plasma inside the object being sterilized to effectively disinfect and sterilize, for example, medical instruments packed in resinous packages and to sterilize foods inside packages, and packages and bags for foods.

The embodiments of the microwave plasma sterilizing device of this invention are described below referring to FIGS. 2 through 5.

Working Example 1

Figure 2:
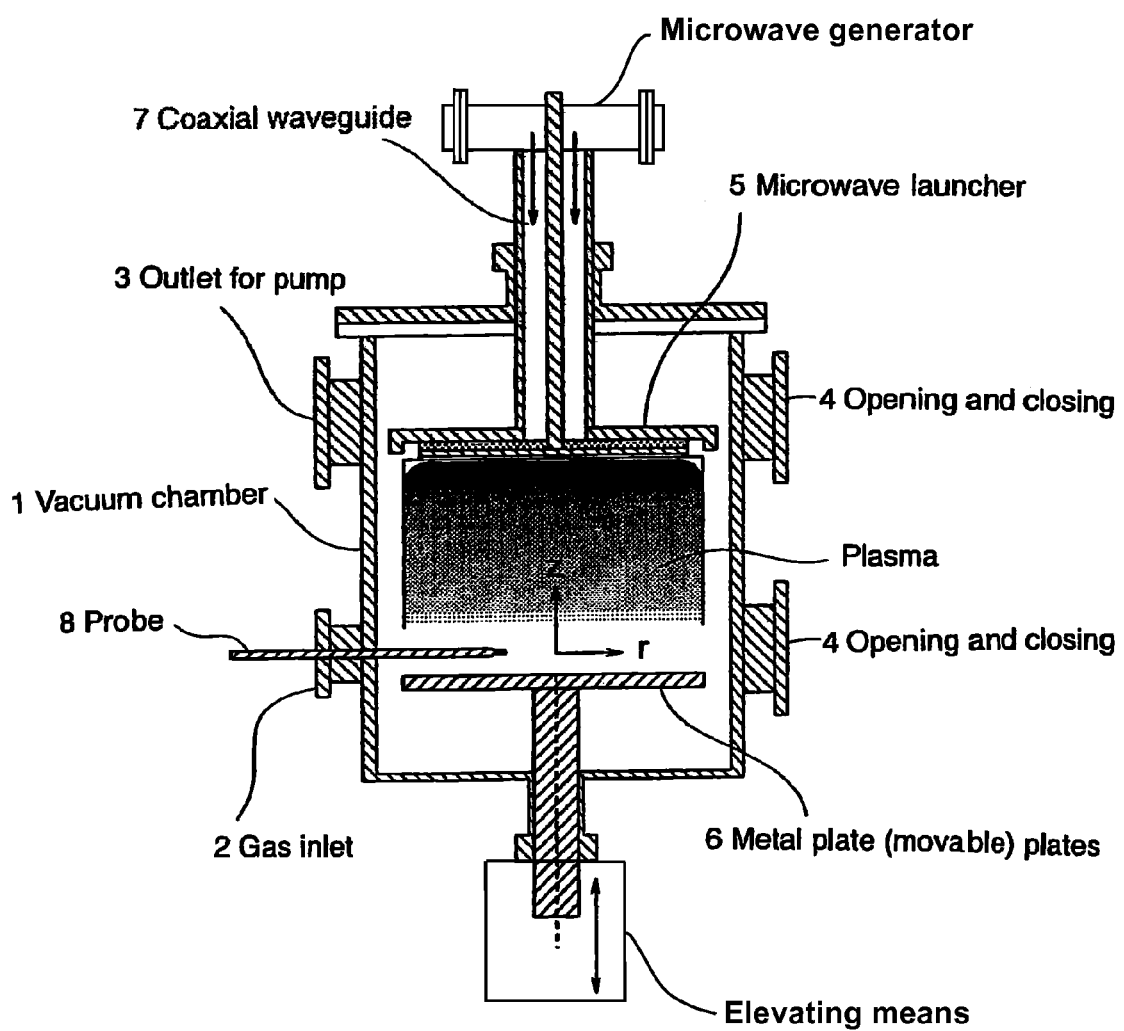
FIG. 2 is an explanatory drawing of a working example of the microwave plasma sterilizing device of this invention.
Figure 3:
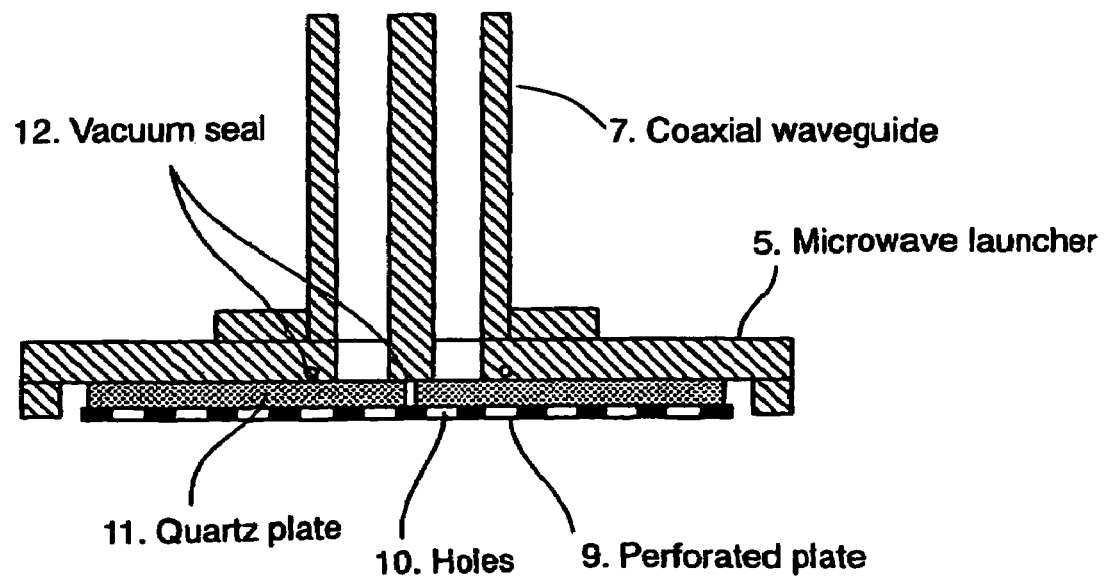
FIG. 3 is an enlarged view of the microwave launcher of the device of this invention.

FIG. 2 shows a working example of the microwave plasma sterilizing device of this invention. FIGS. 2 and 3 illustrate and identify stainless steel cylindrical vacuum chamber 1, gas inlet 2, outlet 3 for the pump, upper and lower opening and closing plates 4, microwave launcher 5, movable metal plate 6, coaxial waveguide 7 for introducing microwaves from an external microwave generator, probe 8 for detecting the condition of the vacuum chamber, perforated plate 9, many holes 10 of a specified diameter perforated through the perforated plate, quartz plate 11, and vacuum seal 12.

The stainless steel cylindrical vacuum chamber 1 of this working example is 500 mm high and has an inside diameter of 250 mm. An aluminum microwave launcher 5 is arranged in the vacuum chamber 1. A movable metal plate 6, 220 mm in diameter, is arranged opposite to the microwave launcher 5. The movable metal plate 6 is connected to an elevating means to allow vertical positional adjustment.

FIG. 3 is an enlarged view of the microwave launcher 5. The microwave launcher 5 has a sandwiched structure where the quartz plate 11, which is 8 mm thick and has an inside diameter of 220 mm, is sandwiched by a stainless steel perforated plate 9. The holes 10 through the perforated plate 9 are 2 mm or 8 mm in diameter. Many holes are drilled through the perforated plate 9. The microwave launcher 5 and the coaxial waveguide 7 are sealed by vacuum seals 12.

A 2.45 GHz microwave oscillator (not shown) with 1.5 kW output transmits microwaves to the microwave launcher 5 after coaxial conversion at the coaxial waveguide 7. In this working example, we used He gas at 1.2 Torr gas pressure to generate plasma. The temperature rise of the vacuum chamber 1 is controlled by converting microwaves from the microwave oscillator into pulses and controlling the pulse time interval while monitoring the internal temperature of the vacuum chamber with the probe 8.

We adjusted the shape of the plasma discharge by changing the distance between the microwave launcher 5 and metal plate 6 and by varying the diameter of the holes of the perforated plate 9. We then optimized the plasma generation by controlling the spatial distribution of the electron field intensity. We confirmed that the volume-wave plasma discharge was diffused to the entire inner space of the vacuum chamber due to the microwaves leaking through the holes in the perforated plate when we adequately adjusted the microwave launcher 5 and the metal plate 6.

Working Example 2

Figure 4:
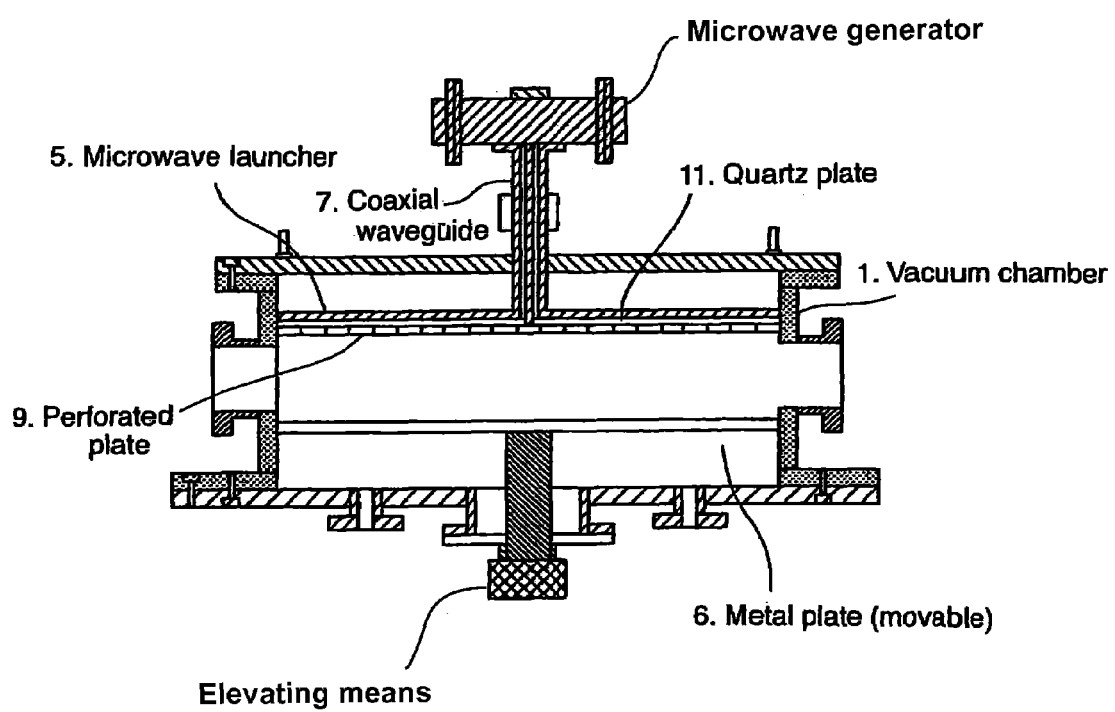
FIG. 4 is an explanatory drawing of another working example of the microwave plasma sterilizing device of this invention.

FIG. 4 shows another working example of the microwave plasma sterilizing device of this invention. The figure depicts the structure of the vacuum chamber of a large-area plasma device. The reference numerals are the same as used in FIGS. 2 and 3. The stainless steel cylindrical vacuum chamber 1 is 350 mm high and has an inside diameter of 600 mm. The microwave launcher 5 is suspended from above in the vacuum chamber 1. The quartz plate 11 is 10 mm thick and has a diameter of 500 mm. The diameter of the holes 10 through perforated plate 9 are 4 mm, 6 mm or 10 mm.

Figure 5:
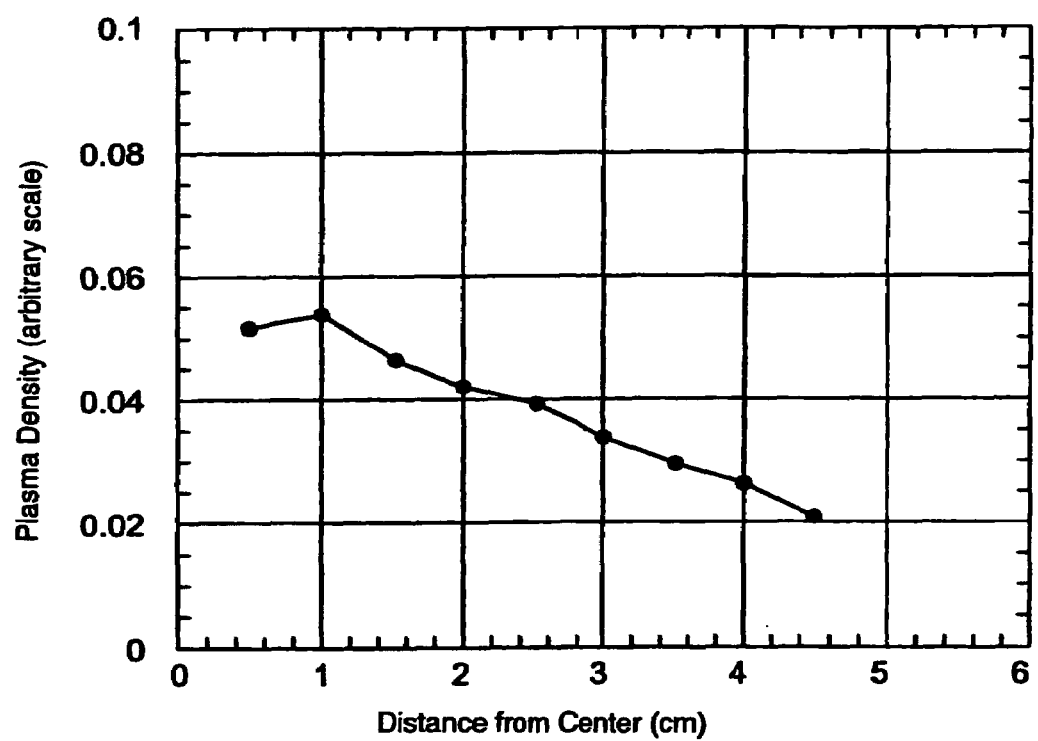
FIG. 5 is a diagram showing the spatial distribution of electron density in volume-wave plasma.

A 2.45 GHz microwave oscillator (not shown) with 1.5 kW output transmits microwaves to the microwave launcher 5 after coaxial conversion at the coaxial waveguide 7. In this working example, we used Ar gas at 74 mTorr gas pressure to generate plasma. As we increased the incident power from 0.2 kW to 1.5 kW, plasma was generated at the center of the launcher 5 and gradually expanded around the launcher's periphery. As shown in FIG. 5, the spatial distribution of the electron density in volume-wave plasma is strong at the center of the launcher 5 and gradually decreases at distances farther away from the center.

An object to be sterilized that was packed in a resinous package was put on the metal plate 6 of the microwave plasma sterilizing device as described above and placed at the center of the cylindrical vacuum chamber 1. The test samples for sterilization were *Bacillus subtilis* and *Bacillus stearothermophilus*, the two most powerful hay bacilli. We found that the number of spores decreased considerably by plasma irradiation.

The results of our sterilization experiments using plasma irradiation with different gas types are reported below.

A sample consisting of *Bacillus stearothermophilus* with a population of $3.0 \times 10^6$ was placed on the centerline of the quartz plate in the vacuum chamber and 20 cm (z axis) away from the quartz plate.

(1) Sterilization in Oxygen Gas

Oxygen gas (100%) was introduced into the vacuum chamber at 60 to 70 mTorr gas pressure and 100 sccm flow rate. Plasma was generated under 750 W incident power and this plasma was used to generate active species with a sterilization effect in the presence of the plasma. The survival curve for spores in the oxygen gas in this experiment is shown in FIG. 6.

Figure 6:
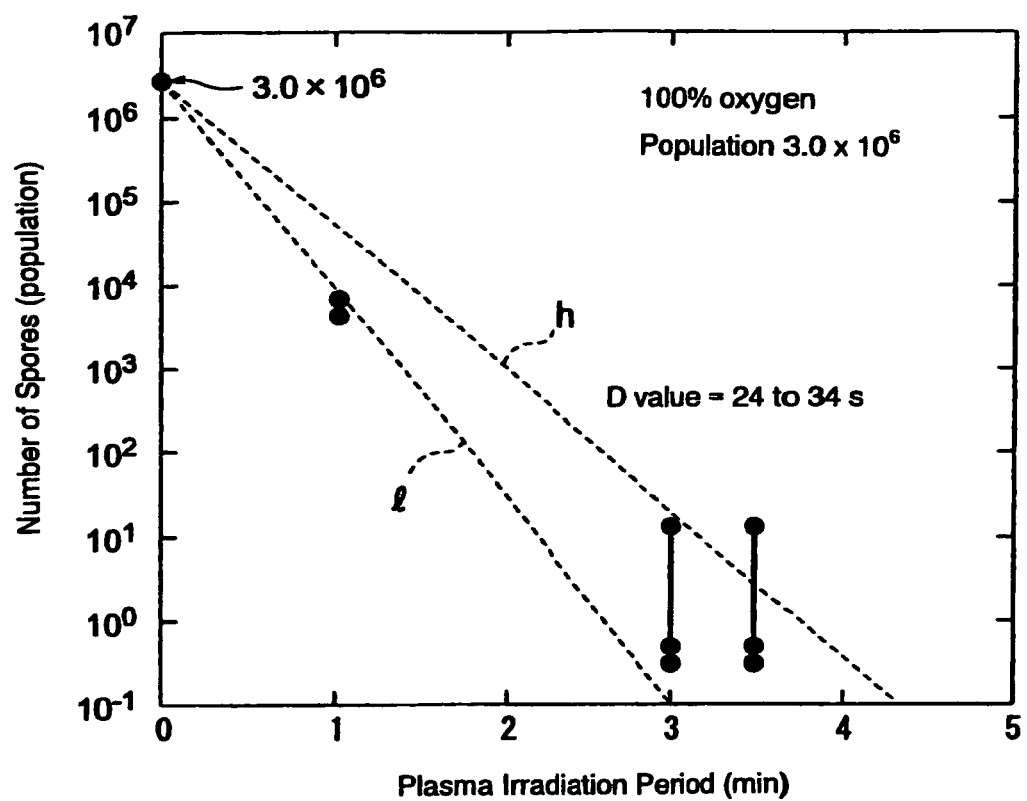
FIG. 6 shows the survival curve for spores in oxygen gas.

In FIG. 6, the number of surviving spores gradually decreases and infinitely approaches zero at longer plasma irradiation periods. The results of multiple experiments show that the number of surviving spores converges on the area between the upper and the lower dotted lines, h and l, respectively. The decimal value (D value=the amount of time required for reducing the population number by one decimal place) was 24 to 34 sec. It is considered to be the effect of sterilization by etching due to oxygen radicals.

(2) Sterilization in Nitrogen Gas

Nitrogen gas (100%) was introduced into the vacuum chamber at 60 to 71 mTorr gas pressure and 100 sccm flow rate. Plasma was generated under 750 W incident power and this plasma was used to generate active species with a sterilization effect in the presence of the plasma. The survival curve for spores in the nitrogen gas in this experiment is shown in FIG. 7.

Figure 7:
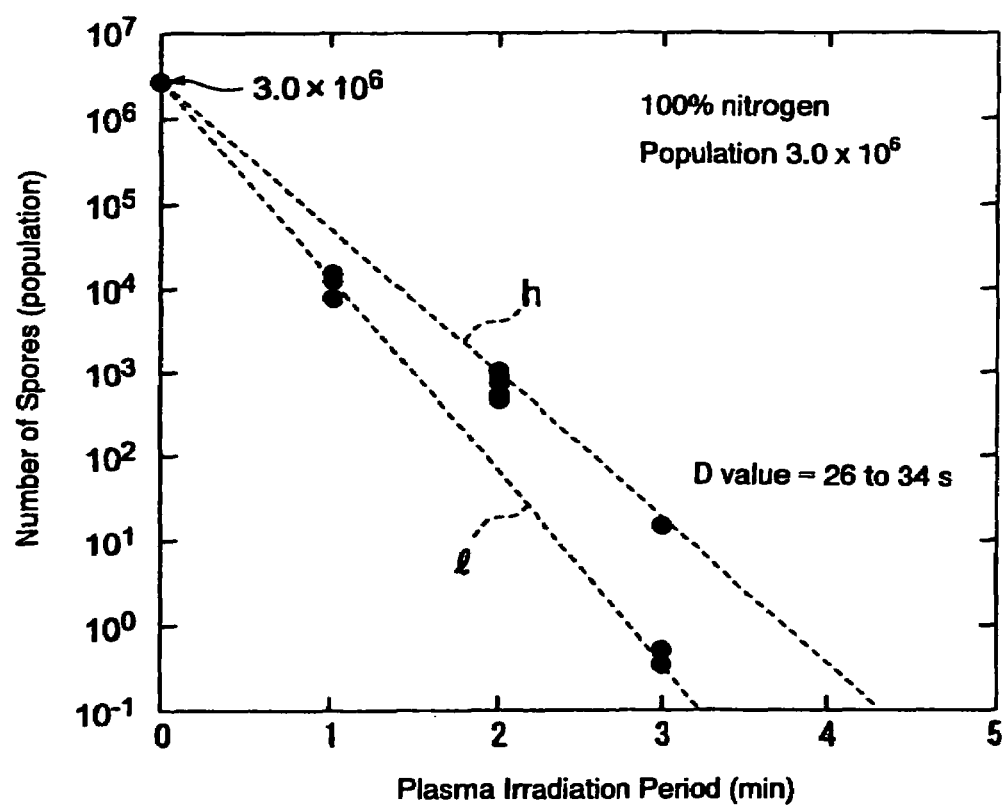
FIG. 7 shows the survival curve for spores in nitrogen gas.

In FIG. 7, the number of surviving spores gradually decreases and infinitely approaches zero as longer plasma irradiation periods. The results of multiple experiments show that the number of surviving spores converges on the area between the upper and the lower dotted lines, h and l, respectively. The decimal value (D value=the amount of time required for reducing the population number by one decimal place) was 26 to 34 sec. It is considered to be the effect of sterilization by ultraviolet rays generated by nitrogen gas.

(3) Sterilization in a Mixture of Oxygen Gas and Nitrogen Gas—Part 1

A mixture of 1 part oxygen gas and with 9 parts nitrogen gas was introduced into the vacuum chamber at 60 to 73 mTorr gas pressure and 10 sccm and 90 sccm flow rate for oxygen and nitrogen, respectively. Plasma was generated under 750 W incident power and this plasma was used to generate active species with a sterilization effect in the presence of the plasma. The survival curve for spores in the mixed gas in this experiment is shown in FIG. 8.

Figure 8:
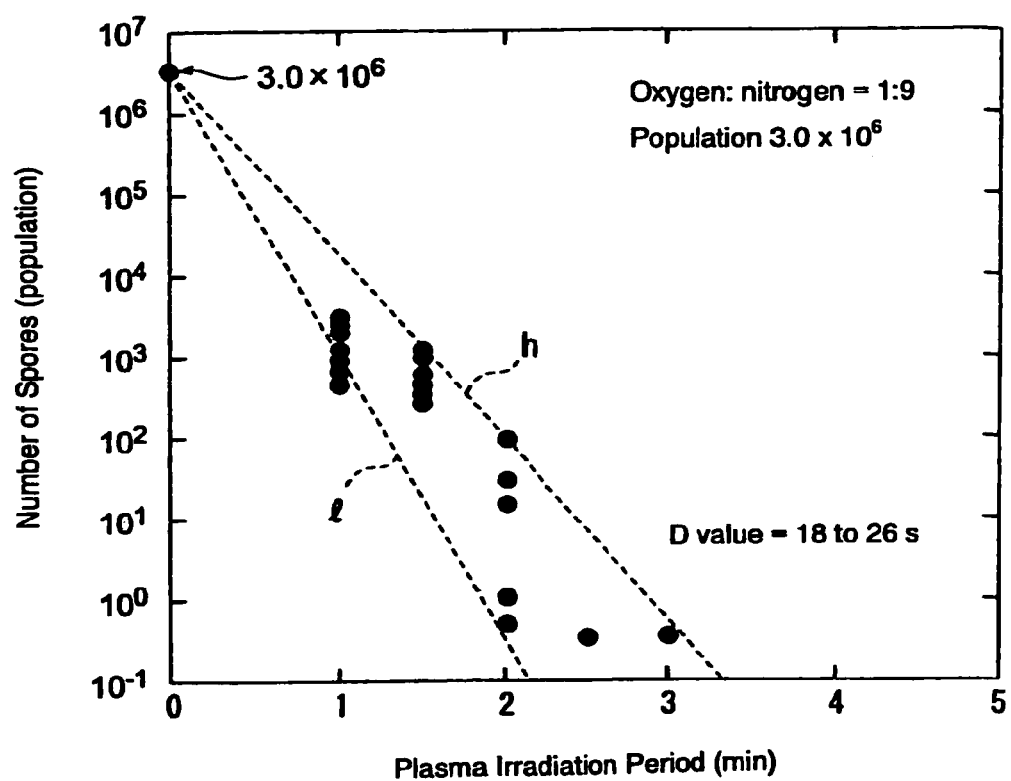
FIGS. 8 and 9 show the survival curves for spores, Parts 1 and 2, respectively, in a mixed gas of oxygen gas and nitrogen gas.

In FIG. 8, the number of surviving spores gradually decreases and infinitely approaches zero at longer plasma irradiation periods. The results of multiple experiments show that the number of surviving spores converges on the area between the upper and the lower dotted lines, h and l, respectively. The decimal value (D value=the amount of time required for reducing the population number by one decimal place) was 18 to 26 sec. It is considered that the effect of sterilization by ultraviolet rays due to the nitrogen gas is added to the effect of sterilization by etching due to oxygen radicals.

(4) Sterilization in a Mixture of Oxygen Gas and Nitrogen Gas—Part 2

A mixture of 1 part oxygen gas and 4 parts nitrogen gas was introduced into the vacuum chamber at 60 to 70 mTorr gas pressure and 20 sccm and 80 sccm flow rate for oxygen and nitrogen, respectively. Plasma was generated under 750 W incident power and this plasma was used to generate active species with a sterilization effect in the presence of the plasma. The survival curve for spores in the mixed gas in this experiment is shown in FIG. 9.

Figure 9:
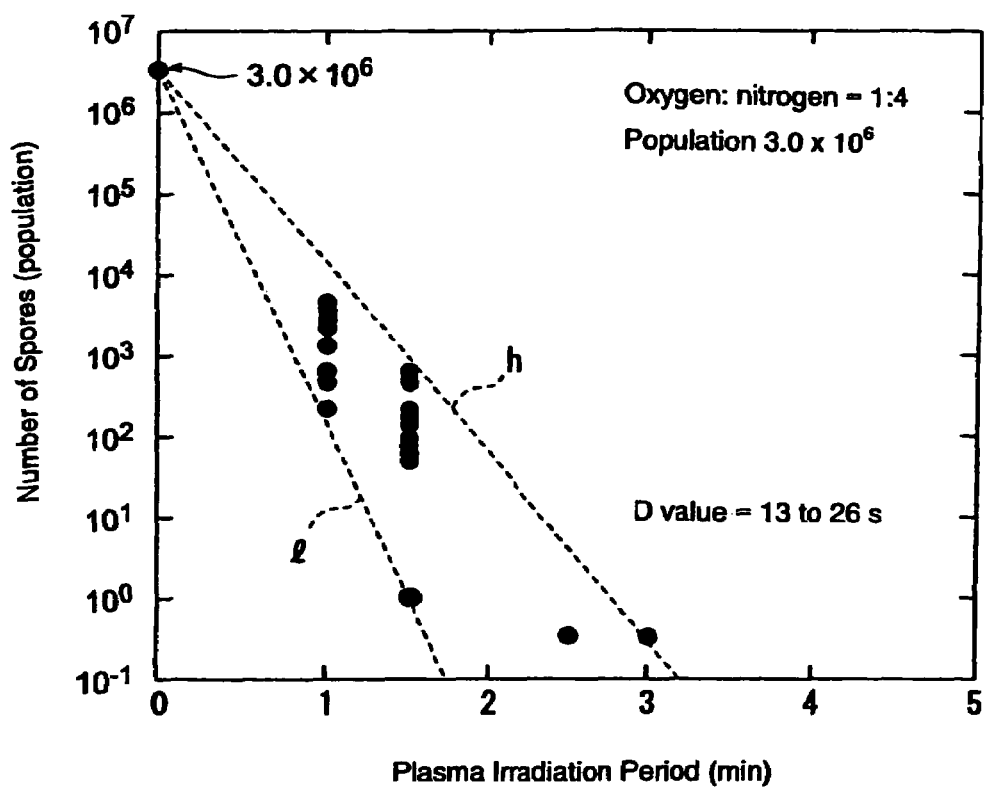

In FIG. 9, the number of surviving spores gradually decreases and infinitely approaches zero at longer plasma irradiation periods. The results of multiple experiments show that the number of surviving spores converges on the area between the upper and the lower dotted lines, h and l, respectively. The decimal value (D value=the amount of time required for reducing the population number by one decimal place) was 13 to 26 sec. It is considered that the effect of sterilization by ultraviolet rays due to nitrogen gas is added to the effect of sterilization by etching due to oxygen radicals. Importantly, an effective sterilization effect is observed in a mixed gas of nearly the same gas mixing ratio as air.

INDUSTRIAL APPLICABILITY

As detailed above, the microwave plasma sterilizing method and device of this invention are applicable to the disinfection and sterilization of medical instruments that require sterilization of the inside of an instrument such as metal medical instruments including catheters and injection devices, glass and resinous medical instruments and vacuum tubes for drawing blood. The microwave plasma sterilizing method and device of this invention are further applicable to the sterilization of foods packed in perforated packages for foods and bags (currently with the exception of liquids).

The invention claimed is:

1. A microwave plasma sterilizing device comprising: a microwave generator for outputting pulsed microwaves and a vacuum chamber with a gas inlet, outlet for pump and opening and closing plates, wherein a microwave inlet for introducing microwave and a microwave launcher of a sandwiched structure where a quartz plate for generating volume-wave plasma is sandwiched by a stainless steel perforated plate are arranged on one side in said vacuum chamber, and a movable metal plate is arranged opposite to said microwave launcher on the other side in said vacuum chamber, wherein said movable metal plate is connected to an elevating means to allow positional adjustment and wherein an object being sterilized is placed between said microwave launcher and said movable metal plate.

2. A microwave plasma sterilizing method implemented by the microwave plasma sterilizing device according to claim 1, comprising the steps of placing an object being sterilized between said microwave launcher and said movable metal plate and generating plasma inside the object being sterilized by microwave-excited volume-wave plasma discharge in gas that produces an active species with a sterilization effect in the presence of plasma and sterilizing the object by said generated plasma.

3. The microwave plasma sterilizing method according to claim 2 wherein said gas that produces an active species with a sterilization effect in the presence of plasma is oxygen gas.

4. The microwave plasma sterilizing method according to claim 2 wherein said gas that produces an active species with a sterilization effect in the presence of plasma is a mixture of helium gas and oxygen gas.

5. The microwave plasma sterilizing method according to claim 2 wherein said gas that produces an active species with a sterilization effect in the presence of plasma is a mixture of argon gas and oxygen gas.

6. The microwave plasma sterilizing method according to claim 2 wherein said gas that produces an active species with a sterilization effect in the presence of plasma is a mixture of oxygen gas and nitrogen gas.

7. The microwave plasma sterilizing method according to claim 6 wherein said mixture of oxygen gas and nitrogen gas consists of 1 part oxygen and 4 parts nitrogen gas.

8. The microwave plasma sterilizing method according to claim 2 wherein said sterilizing object is an object packed in a perforated resinous package.

9. The microwave plasma sterilizing method according to claim 2 wherein said sterilizing object is a medical instrument packed in a perforated plastic package.

10. The microwave plasma sterilizing method according to claim 2 wherein said volume-wave plasma discharged in said gas is excited by pulsed microwaves.

* * * * *